United States Patent [19]

Mochizuki et al.

[11] Patent Number: 4,696,672
[45] Date of Patent: Sep. 29, 1987

[54] BLADDER CONTROL DEVICE

[75] Inventors: Masatsugu Mochizuki, Shiga; Masanobu Jige; Yoshihiro Umemura, both of Kyoto all of Japan

[73] Assignee: Unitaka Ltd., Hyogo, Japan

[21] Appl. No.: 912,173

[22] Filed: Sep. 22, 1986

Related U.S. Application Data

[63] Continuation of Ser. No. 704,001, Feb. 21, 1985, abandoned.

[30] Foreign Application Priority Data

Feb. 23, 1984 [JP] Japan .................................. 59-33981
Apr. 6, 1984 [JP] Japan .................................. 59-70525

[51] Int. Cl.4 ........................................... A61M 5/325
[52] U.S. Cl. ..................................... 604/128; 604/265
[58] Field of Search ................... 604/27, 128, 129, 265

[56] References Cited

U.S. PATENT DOCUMENTS

| | | | |
|---|---|---|---|
| 2,602,448 | 7/1952 | McKenna | 604/128 |
| 2,860,636 | 11/1958 | Seitchik et al. | 604/128 |
| 3,503,401 | 3/1970 | Andersen et al. | 604/129 |
| 3,604,420 | 9/1971 | Vaillancourt | 128/275 |
| 4,084,593 | 4/1978 | Jarund | 128/295 |
| 4,515,593 | 5/1985 | Norton | 604/265 |
| 4,539,234 | 9/1985 | Sakamoto et al. | 604/265 |

FOREIGN PATENT DOCUMENTS 514765 12/1930 Fed. Rep. of Germany .

Primary Examiner—C. Fred Rosenbaum
Assistant Examiner—Sherri E. Vinyard
Attorney, Agent, or Firm—Wenderoth, Lind & Ponack

[57] ABSTRACT

A bladder assist device for maintaining natural drainage by a repetition of expansion and contraction of a bladder even when a urethral catheter is embedded in the bladder which includes a pressure control chamber containing a concentric-type siphon tube connected to a urethral catheter at a particular part, the pressure control chamber having a pressure control hole sealed by an air flow restricting filter.

5 Claims, 4 Drawing Figures

BLADDER CONTROL DEVICE

This application is a continuation of now abandoned application Ser. No. 704,001 filed Feb. 21, 1985.

FIELD OF THE INVENTION

The present invention relates to a bladder assist device which is capable of maintaining natural drainage by expansion and contraction of the bladder, even when a urethral catheter is embedded in the bladder.

BACKGROUND OF THE INVENTION

A patient suffering from spinal cord injury, encephalorrhagia or encephalomalacia, a patient after an operation or a bedridden old man is liable to show symptoms of dysuria, urine incontinence and the like. In such a case, a urethral catheter has been widely used for ensuring a smooth urinary passage and maintaining or improving the kidney function, or preventing the leakage of urine. However, in the case of a continuous drainage method wherein the urethral catheter is embedded in the body for a long period of time, the bladder is always contracted with the result that the normal drainage function obtained from a repetition of expansion and contraction is not possible. Generally, man has the following drainage mechanism; storing urine in the bladder, stimulating an inherent receptor in the bladder wall by expansion of the bladder wall due to repletion with urine, stimulating the drainage center of the cerebrum from the myelon through the brain stem which causes contraction of the bladder wall, relaxing the muscle group of the pelvis bottom, relaxing the urethral sphincter muscle and urinating. On the other hand, the drainage mechanism is prevented in a patient having a catheter embedded in the bladder, since the most essential process in the drainage mechanism, i.e. the repletion with urine and the stimulation of the receptor with the expansion of the bladder wall, is lost. In other words, the function of the bladder is completely stopped and the bladder becomes a passage for urine or a collecting space of urine. In such a case, there are medical and physiological problems which have been discussed for a long period of time. Three of these problems can be summarized as follows: First, since a patient is laid on one's back and the lowest point of the bladder becomes a dead space which gathers a small amount of residual urine, which, in turn, becomes a good culture medium for microbes which intrude into the bladder from inside or outside of the catheter tube, the bladder is a source of cystitis, pyelitis or pyelonephritis. Second since a tip of the ballon catheter inserted into the bladder always presses on a part of the contracted bladder wall, which results in an ulcer due to a poor circulation of the blood and then a necrosis which is known as "Foley tip necrosis", the diseased tissue becomes a suitable entrance for microbes, which may very likely cause cystitis to develop. Third, since the bladder function is completely prevented by use of the catheter, recovery of the bladder function becomes more delayed after prolonged use of the catheter. In the case of a patient suffering from ischuria after an operation on a pelvis, a spinal cord injury or a cerebrum blood vessel disease, it should be noted that the patient having used the embedded catheter for a long period of time has difficulty in training the bladder, even though training of the bladder is usually started in the subacute period (a recovering period of the drainage function).

In order to solve the above problems associated with the long-term indwelling of the catheter, U.S. Pat. Nos. 3,503,401 and 4,084,593 proposed a drainage control system and a bladder training apparatus, respectively, in which outlets of the urethral catheter are connected to a siphon. Since these apparatuses allow the bladder to alternately repeat expansion and contraction while the urethral catheter is embedded in the body, they seem to be useful for solving the above problems. However, problems still remain to be solved for a clinical use of these systems.

For example, the drainage control system described in U.S. Pat. No. 3,503,401 is an open system in which a drainage tube leading to a collection container from the urethral catheter is opened to the air. In this system, there is a period of transient pressure reduction in the drainage tube which arises right after siphoning, whereby a back flow can be produced from the air to the bladder. The back flow may be stronger than in the conventional continuous drainage method with the indwelling urethral catheter and may contain the microbes associated with dust in the air or from the polluted urine in the form of bubbles. There is a high probability that the invasion of microbes from the air to the bladder will cause an infection due to the microbes. Once the microbes invade the bladder they begin to proliferate exponentially in number. It would be more desirable, however, to reduce the number of microbes to as few as possible. Even though this system contemplates dilution and discharge of the microbes invaded into the bladder, there is no provision for preventing the invasion of the microbes, which is the major reason why the system is not practical for clinical use. This problem is also present where the invasion of microbes is from an air tube. A second problem is that a part forming the siphon tube is so thin and particularly so long that the liquid in the siphon tube can not be drained away completely and liquid columns are formed within the tube. In such a case, the siphon tube does not work well afterward. For example, if the air between two liquid columns is at low pressure, the siphon tube begins to work before the bladder fills up with urine.

In the bladder training apparatus to U.S. Pat. No. 4,084,593, the drainage cycle is very long in comparison with the usual drainage cycle. The intermittent autodrainage method accomplished by the above apparatus is superior to the conventional continuous drainage method in view of an anti-infection effect because the intermittent process completely drains urine away during a time in which the invaded microbes do not proliferate sufficiently. However, the microbes can proliferate enough to result in cystitis if the drainage cycle is long enough to store urine a sufficient length of time. Particularly, a serious illness such as pyelonephritis can be developed if during the intermittent drainage, the bladder is temporarily filled up. The above mentioned problem is knonw to persons in the medical field of urology and is described in MODERN MEDICINE, by Nishiura, December, page 22 (1979). It has been found that intervals of drainage should be done preferably within 3 hours, and at the most within 5 hours. However, in the bladder training apparatus of the above patent, a volume of a pressure chamber which is located below the bladder is larger than that of the bladder and a lower end of the inverse U-shaped siphon tube in the chamber is inserted close to the bottom of the chamber as shown in the specification, particularly in FIG. 1 and FIG. 2 (U.S. Pat. No. 4,084,593 does not disclose the relative sizes of the parts of the apparatus excepting the inside diameter of the siphon tube, but the disclosure does state that the relative location of the various components is as shown in the drawings). The amount of liquid to be drained by one siphoning, in other words, the amount of liquid to be filled before the next siphoning, is nearly equal to the total of the volume of the bladder ($V_1$) and the volume of the above chamber above the lower end of the siphon tube ($V_2$). The additional $V_2$ which must be accommodated in the drain cycle causes the intervals of drainage to be longer than the usual cycle. From this point of view, it would be desirable to maintain the depth of the siphon tube of the above mentioned pressure chamber as shallow as possible. However, if the depth of the siphon tube is made shallow, the waste fluid above the lower end of the siphon tube will be drained away and the siphoning will be stopped before the whole content of the bladder is drained away due to the large flow-pressure loss which will occur in the thin inside diameter of the catheter. The above problem is difficult to solve due to the interdependency between $V_1$, $V_2$, the inside diameter of the catheter and the inside diameter of the siphon tube.

This problem is solved for the first time by the present invention in which a pressure control hole sealed by a filter having a property of restricting air flow is equipped with a pressure chamber, which is described hereinafter. On considering this point, a tube of the bladder training apparatus in U.S. Pat. No. 4,084,593 corresponding the air control tube of the present invention is connected to a collection container or an air-containing bag and therefore the air is free to flow, which can not solve the abovementioned problem. As described hereinbefore, the bladder training apparatus of U.S. Pat. No. 4,503,401 is useful for short term training of a bladder, but it is not suitable for long term training since it does not have a sufficient anti-infection capability to prevent infections from becoming started.

Also, U.S. Pat. Nos. 2,602,448 and 2,860,636 disclose a tidal drainage and an irrigating unit in which expansion and contraction of the bladder is alternately repeated according to the siphon principle. These apparatuses are different from the present invention in the following points.

Both apparatuses are bladder irrigating units, in which the irrigating mechanism comprises repetition of the following cycle; an irrigating agent flows into the inside of the apparatus and from a tube connected to the bottom of the apparatus through a catheter into a bladder, the inside pressure of the bladder rises and the liquid surface in the apparatus rises as the bladder is filling up with the agent and urine, and then when the liquid in the apparatus reaches a certain point the siphoning is begun and the content in the bladder is drained. Some differences between the apparatuses of the above U.S. Patents and the device of the present invention are that each apparatus has the inlet for the irrigating agent at the top of the apparatus and the connection inlet to the catheter is located below the lower end of the inlet of the outer siphon tube. If the connection inlet is located above the lower end of the outer siphon tube, air would flow into the bladder, which is undesirable in the operation of each apparatus of these U.S. Patents. On the other hand, in the apparatus of the present invention, a connecting nozzle connected to the catheter should be located above the lower end of the inlet of the siphon tube for achieving the following two objectives:

(1) so that no material flows into the bladder from the device; and (2) so that residual urine in the bladder is decreased to as little as possible after siphoning.

SUMMARY OF THE INVENTION

The present invention provides a bladder assist device which comprises;

(a) a urethral catheter 2 embedded in a bladder, (b) a pressure control chamber 3 containing a concentric-type siphon tube 10, which is connected either directly or through a connecting tube 4 to the outlet of said urethral catheter 2 at a location between an upper portion of an inner tube 11 of said concentric-type siphon tube 10 and a lower end of an outer tube 12 of said concentric-type siphon tube 10 and below a place of an insertion end of the catheter 2 embedded in the bladder, in which the upper portion of the inner tube 11 of the concentric-type siphon tube 10 is located above the place of the insertion end of the catheter 2, (c) a urine collecting chamber 5 located below said pressure control chamber 3, which is connected to the inner tube 11 of the concentric-type siphon tube 10, and (d) a pressure control hole 14 sealed by a filter 15 having a property of restricting air flow located in said pressure control chamber 3 above the upper portion of the inner tube 11 of the concentric-siphon tube 10.

BRIEF DESCRIPTION OF THE DRAWINGS

The drawings show an embodiment of the bladder assist device of the present invention.

DETAILED DESCRIPTION OF A PREFERRED EMBODIMENT

Figure 1:
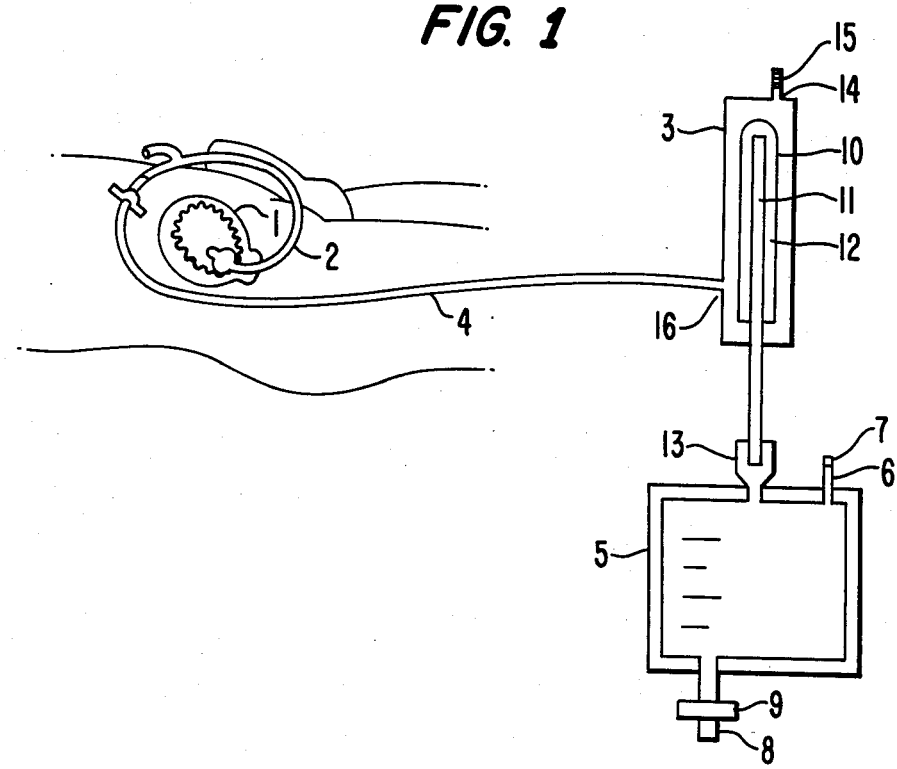
FIG. 1 is a cross sectional view of the apparatus of the present invention.
Figure 2:
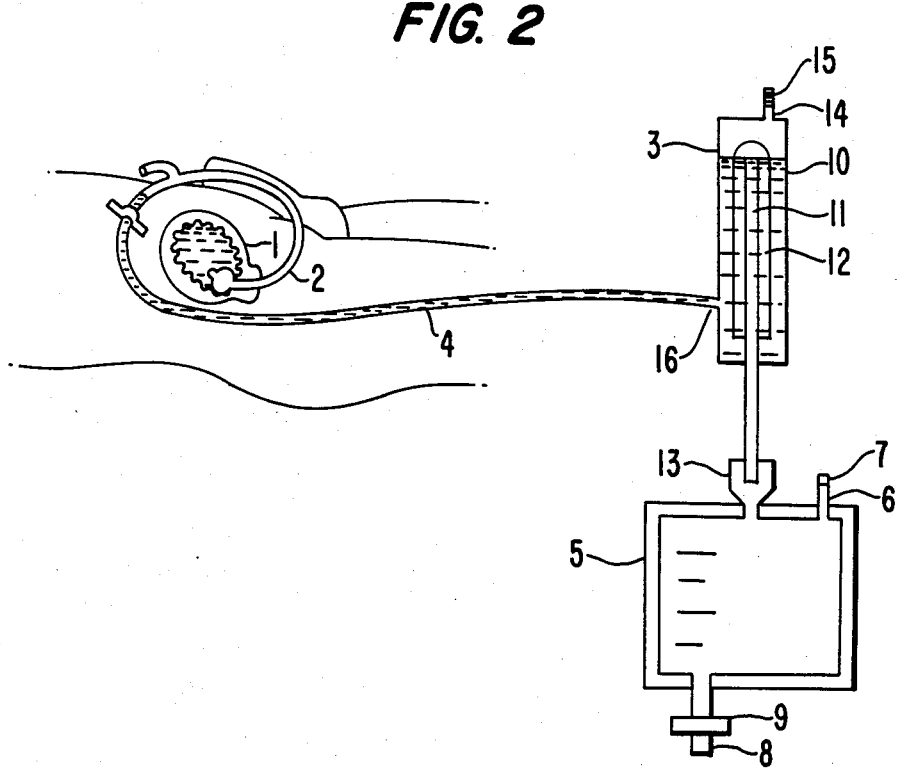
FIG. 2 shows a cross sectional view in which the bladder is filled with urine before siphoning.
Figure 3:
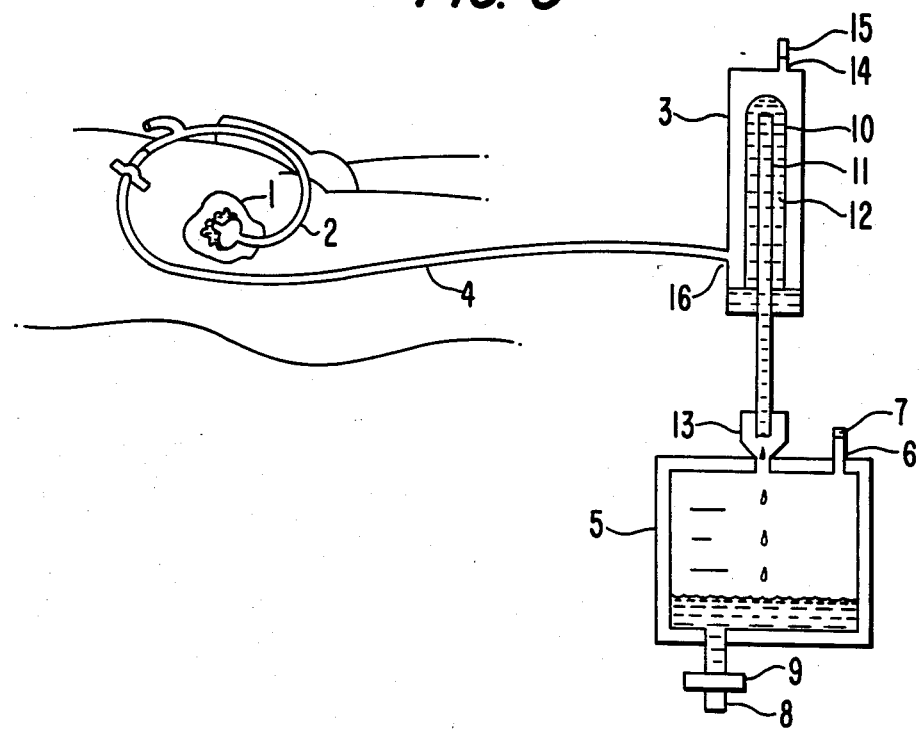
FIG. 3 shows a cross sectional view just before finishing the siphoning, when the bladder is already emptied.

In the drawings, numbers indicate parts of the invention as follow: a bladder 1, a urethral catheter 2, a pressure control chamber 3, a tube 4 connecting the outlet of the urethral catheter 2 to the pressure control chamber 3 (or a connecting tube 4), a urine collecting chamber 5 located below the pressure control chamber 3, a vent hole 6 in the urine collecting chamber 5, a microporous filter 7 for sterilization of air attached to the vent hole 6, an outlet tube 8 in the urine collecting chamber 5, a stopper 9 in the outlet tube 8, a concentric-type siphon tube 10 contained in the pressure control chamber 3, an inner tube 11 of the concentric-type siphon tube 10, an outer tube 12 of the concentric-type siphon tube 10, a non-return device 13 attached to the entrance part of the urine collecting chamber 5, a pressure control hole 14 in the pressure control chamber located above the upper portion of the concentric-type siphon tube 10, a filter 15 having a property of restricting air flow for sealing the pressure control hole 14 and connection means comprising a connecting nozzle 16 attached to the connecting tube 4.

Constructional features of the device of the present invention include the concentric-type siphon tube 10 which allows the device to become compact and easily used in comparison with conventional apparatuses using an inverse U-shape siphon tube, and the pressure control hole 14 sealed by the filter 15 having an air flow regulating property and which is located above the upper portion of the concentrictype siphon tube 10 contained in the pressure control chamber 3. In the conventional apparatus, since the inside diameter of the urethral catheter is generally thin (2 to 3 mm) and long enough to have a large pressure loss when urine flows in the catheter, a supply rate ($Q_1$) from the bladder 1 to the pressure control chamber 3 does not catch up with a drain rate ($Q_2$) of the pressure control chamber 3 through the siphon tube 10 during siphoning, whereby the pressure control chamber is liable to become emptied before the bladder 1 is completely emptied. In the present invention, the pressure control hole 14 is sealed by the air flow regulating filter 15 which reduces the siphoning rate and allows a reduced pressure which arises on siphoning in the system to be maintained for a long time. Accordingly, it is possible for $Q_1$ to approach $Q_2$ for the first time. This means that it becomes possible for the removal volume $V_2$ of the pressure control chamber 3 ( a volume between the lower end of the outer tube 12 of the concentric-type siphon tube 10 and the upper portion of the inner tube 11 of the concentric-type siphon tube 10) to be reduced to a minimum, which allows the drainage cycle to be shortened and approach that of a natural drainage cycle. In other words, one advantage of using the air flow regulating filter 15 of the present invention is that the drainage cycle can be shortened and it is possible to drain urine away from the bladder before the increase in number of the microbes occurs, even when the microbes invade the bladder from the outside or inside of the catheter tube. Also, since the filter 15 also fulfils a role of preventing microbe invasion into the pressure control chamber 3 pollution by microbes from the outside of the system due to a reduced pressure in the system on siphoning can be avoided. Furthermore, because the reduced pressure in the system can be maintained for a long time, it is possible to reduce the distance between the upper end and the lower end of the concentric-type siphon tube, thus making miniaturization of the apparatus possible.

The air flow regulating filter 15, preferably, has a flow rate of about 10 to about 20,000 ml/min. Flow rates less than 10 ml/min have an undesirable effect on siphoning, and preferred flow rates, therefore, are at least 10 ml/min, desirably at least 50 ml/min, particularly at least 100 ml/min. Flow rates more than 20,000 ml/min make the siphoning very fast so as to empty the pressure control chamber 3 before the bladder is emptied, and the preferred flow rates, therefore, are not more than 20,000 ml/min, desirably not more than 10,000 ml/min, particularly not more than 5,000 ml/min, and more particularly not more than 1,000 ml/min. The air flow rate is the volume of air filtrated per unit of time using non-particulate air at 20° C. under a pressure of 0.07 kg/cm² (1 PSI). Various kinds of air flow regulating filters 15 can be prepared by controlling the pore size, the porosity and the cross-sectional area of the filter. A preferred pore size is less than 1 micron in order to limit the invasion of the microbes to as few as possible. The types of materials used for the forms of the air flow regulating filter 15 are not limited. Generally, any membrane filter, sponge, unwoven fabric, cotton sealer and the like which is prepared from regenerated cellulose, nitrocellulose, acetate cellulose, polyvinylidene fluoride, polytetrafluoroethylene and the like can be employed.

The air flow regulating filter 15 can be equipped on the pressure control chamber 3 at a location above the upper portion of the concentric-type siphon tube 10 so that it is not polluted by urine which may rise up to the upper portion of the siphon tube 10 in the pressure control chamber 3. Preferably, the filter 15 is installed on the chamber 3 at a sufficient height to avoid a sudden rise of the liquid surface which may occur due to a sudden pressure change in the abdominal region when a patient coughs or sneezes. A barrier may also be installed in the pressure control chamber 3 to prevent a sudden rise of the liquid from contacting the filter.

Figure 4:
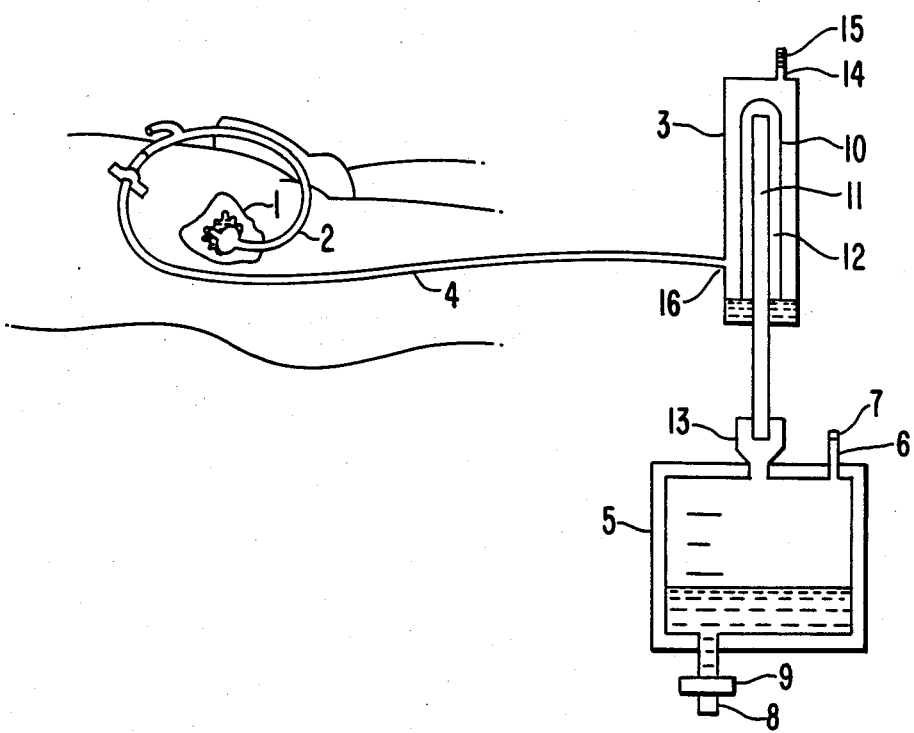
FIG. 4 shows a cross sectional view in which the siphoning is finished.

The inner tube 11 of the concentric-type siphon tube 10 should have an inside diameter of 1 to 10 mm, and preferably 3 to 7 mm. Inside diameters of less than 1 mm are not desirable because, after siphoning, there is a high probability that short liquid columns will be trapped in the tube. On the other hand, inside diameters of more than 10 mm have an undesirable effect on siphoning. The outer tube 12 of the concentric-type siphon tube 10, preferably, has an inside diameter such that an annular cross sectional area between the outside wall of the inner tube and the inside wall of the outer tube is nearly equal to the inside cross sectional area of the inner tube 11. The lower end of the outer tube 12 of the concentric-type siphon tube 10, preferably, has a construction as shown in FIG. 4, FIG. 6, FIG. 7 and FIG. 8 of U.S. Pat. No. 2,602,448. The volume of the pressure control chamber 3 is, preferably, from 50 to 150 ml, and the content volume $V_2$ between the lower end of the outer tube 12 and the upper portion of the inner tube 11 of the concentric-type siphon tube 10 in the pressure control chamber 3 is preferably less than 100 ml. The amount of urine produced by an adult man is about 1,500 ml/day and, when the content ($V_1$) of the bladder is set to about 200 ml, the amount of urine, ($V_1-V_2$), drained by one siphoning process becomes about 200 to 300 ml, whereby drainage can be conducted 5 to 7 times a day, or once in 3 to 5 hours.

The capacity of the urine collecting container 5 is about 2,000 ml which is equal to the maximum amount of urine produced by a patient per day. A preferred type of container 5 is a conventional closed-type urine bag comprising a microbes non-ascending device or drip chamber 13 at the entrance of the bag, a vent hole 6 having a microporous filter for sterilization 7, and a drain 8 to remove urine from the bottom of the bag.

The urethral catheter 2 which can be used in the present invention is preferably a Foley balloon catheter which is suitable for embedding in the body for a long period of time. Other examples of suitable catheters include a double balloon catheter and a different shaped balloon catheter which are expanded at the prostate part in order to prevent a leakage of urine between the outside wall of the catheter and the urethral mucosa membrane. Also, a three way balloon catheter which is equipped with an inlet for a disinfectant agent for irrigating the bladder can be employed, whereby the disinfectant agent can be continuously introduced by gravity into the bladder to irrigate the bladder automatically without a complicated treatment as in the prior art.

In the bladder assist device of the present invention, the relative locations of the various parts of the device are further described in detail. When the urethral catheter 2 is embedded in the bladder, the height between the insertion end of the catheter 2 and the upper portion of the inner tube 11 of the concentric-type siphon tube 10 can be varied within the range of 0 to 100 mm since a water column of 100 mm exerts a pressure nearly equal to the pressure filt by the usual person when the bladder is full. If the pressure is too high in comparison with a necessary pressure, a patient who suffers from the atonic nervous bladder is forced to excessively expand the bladder wall and thus destroy the inherent receptor. When the urethral catheter 2 is embedded in the bladder, the height difference between the insertion end of the catheter 2 and the connecting nozzle 16 of the pressure control chamber 3 is preferably from 50 to 200 mm, which is much smaller than the conventional height. The height difference between the lower portion of the outer tube 12 of the concentric-type siphon tube 10 in the chamber 3 and the entrance of the urine collecting chamber 5 is generally from 100 to 300 mm.

The materials used for the device of the present invention are not limited. Examples of the materials include an injection molding hard plastic such as polycarbonate, polyacrylonitril-styrene copolymer; or a soft plastic having flexibility such as soft polyvinylchloride.

In the present invention, the urethral catheter 2 can contain an antimicrobial agent which is gradually released from the urethral catheter. All urethral catheters which can gradually release the antimicrobial agent can be employed in the present invention. The urethral catheter is generally constructed from materials such as natural rubber and silicone rubber. The antimicrobial agent is combined with the rubber either in the manufacturing process or in a later step after manufacturing the rubber. Also, the agent may be coated to, absorbed into or physically combined with the rubber. When natural rubber is used, the urethral catheter can be manufactured from dip molding an antimicrobial latex composition comprising a biguanide compound or a salt thereof, an acridine compound or a salt thereof, a quaternary ammonium salt compound, or a cation-type antimicrobial agent of other known antibiotics in a natural rubber latex (Japanese Patent Application Ser. Nos. 104572/1983, 148454/1983 and 188942/1983 which are filed by the present applicant). When silicone rubber is used, a catheter may be obtained from combining the above cation-type antimicrobial agent with silicone rubber at a step of mastication, and extrusion molding or compression molding (Japanese Patent Application Ser. No. 188940/1983) or a catheter may be obtained by forming an active coating layer of an antibiotic on the inside or outside of the silicone rubber catheter which is commercially available, and bonding the antibiotic by means of an ionic bond (Japanese Pat. Publn. (unexamined) No. 195471/1982, EP Publn. (unexamined) No 65884, or U.S. Ser. No. 382,734 (May 27, 1982) which are filed by the present applicant) can also be employed in the present invention. Other catheters which may be used include catheters formed by hydrophilic treating of the surface of a natural rubber catheter or a silicone rubber catheter, or by forming a hydrophilic coating layer which is dipped in an antimicrobial agent solution containing isozin and the like to absorb the antimicrobial agent physically.

The present device provides the constant repetition of expansion and contraction of the bladder at a constant rate without using any complicated machines, electric power or electric control systems even when the catheter is embedded in the bladder, whereby maintenance of the bladder function or recovery training of the bladder function can be easily conducted in comparison with the conventional continuous drainage method and the incidence of urinary tract infection can be remarkably reduced. The present invention has the following technical effects:

(1) A reduction in the number of the microbes invading the bladder from the outside by using a urethral catheter which gradually releases an antimicrobial agent;

(2) Prevention in the storage of residual urine and the increase of microbes which otherwise lead to cystitis by using periodic compelled irrigation or rinse treatment (repeated every 5 hours, preferably within every 3 hours);

(3) Avoidance of an outbreak of cystitis produced by indwelling catheters which do not conform to the bladder wall, commonly called "Foley tip necrosis" a syndrome which usually occurs from pressing the contracted bladder wall with the pointed end of the catheter;

(4) Prevention of atrophy of the bladder wall muscle which is observed in a contracted bladder and an increase in resistance against infections, such is observed in a normal bladder; and (5) A reduction in the risk of invasion of microbes through the catheter tube from outside by using a process of repletion of the bladder without a reduced pressure in contrast to the conventional continuous drainage method.

The device of the present invention is effective on a patient suffering from a spinal cord injury, encephalorrhagia, encephalomalacia, or drainage trouble or urine incontinence of a patent after an operation or a bedridden old man. In the case of a patent suffering from a neurogenic bladder as a result of a spinal injury, the period for indwelling of the catheter took for one to 2 months in the conventional continuous drainage method, but in the present invention the period of indwelling of the catheter is shortened to about 2 weeks without urethral infection. In the present invention the training of the bladder can begin during the acute period to the subacute period, which has a significant effect on rehabilitation. When the device of the present invention was used for a bedridden old man, diseases such as cystitis or fever were not developed even after 2 months and the bedridden old man did not suffer from unpleasant conditions such as diaper rash.

What is claimed is:

1. A bladder assist device comprising:
   a urethral catheter adapted to be embedded in a bladder of a patient;
   a pressure control chamber having an upper end, a lower end and a concentric-type siphon tube therein between said upper end and said lower end, said siphon tube including an inner tube having an open end at an upper portion thereof and an outer tube around said inner tube, said outer tube having a closed upper end located above said inner tube and said outer tube having an open end at a lower end thereof spaced above said lower end of said pressure control chamber, said pressure control chamber having connection means connecting said pressure control chamber to said urethral catheter, said connection means connected to an opening in said pressure control chamber at a position between said open end of said upper portion of said inner tube and said open end of said lower end of said outer tube, said connection means also being vertically below a point at which said urethral catheter is embedded in the bladder of a patient and said open end of said upper portion of said inner tube being located at a position vertically above a point at which said urethral catheter is embedded in the bladder of a patient, said inner tube having the other end thereof located outside of said pressure control chamber;

a chamber connected to said other end of said inner tube for collecting urine passed through said concentric-type siphon tube; and an air flow regulating filter disposed in an opening located in said pressure control chamber at a position above said upper portion of said inner tube.

2. The bladder assist device of claim 1, wherein said filter controls air flow therethrough at about 10 to about 20,000 ml/min.

3. The bladder assist device of claim 1, wherein said inner tube has an internal diameter of 1 to 10 mm.

4. The bladder assist device of claim 1, wherein said inner tube has an internal diameter of 3 to 7 mm.

5. The bladder assist device of claim 1, wherein said urethral catheter is of a type which gradually releases an antimicrobial agent.

* * * * *